United States Patent
Zhang et al.

(10) Patent No.: US 10,578,522 B2
(45) Date of Patent: Mar. 3, 2020

(54) VENTILATION SYSTEM FOR IMPROVING INDOOR AIR QUALITY, HVAC SYSTEM COMPRISING THE SAME AND PROCESS THEREOF

(71) Applicants: Wei Zhang, Bellevue, WA (US); Zhaofeng Chen, Hangzhou (CN)

(72) Inventors: Wei Zhang, Bellevue, WA (US); Zhaofeng Chen, Hangzhou (CN)

(73) Assignee: Hangzhou Long Beach Technology Co. Ltd., Hangzhou (CN)

( * ) Notice: Subject to any disclaimer, the term of this patent is extended or adjusted under 35 U.S.C. 154(b) by 469 days.

(21) Appl. No.: 15/615,821

(22) Filed: Jun. 6, 2017

(65) Prior Publication Data

US 2017/0356670 A1     Dec. 14, 2017

(30) Foreign Application Priority Data

Jun. 8, 2016   (CN) .......................... 2016 1 0437764

(51) Int. Cl.
| | |
|---|---|
| F24F 11/00 | (2018.01) |
| G01N 1/26 | (2006.01) |
| F24F 12/00 | (2006.01) |
| F24F 11/74 | (2018.01) |
| F24F 110/50 | (2018.01) |
| F24F 110/70 | (2018.01) |

(52) U.S. Cl.
CPC ................ G01N 1/26 (2013.01); F24F 11/74 (2018.01); F24F 12/006 (2013.01); F24F 2110/50 (2018.01); F24F 2110/70 (2018.01); Y02B 30/563 (2013.01)

(58) Field of Classification Search
CPC ...... F24F 11/74; F24F 12/006; F24F 2110/50; F24F 2110/70; G01N 1/26; Y02B 30/563
See application file for complete search history.

(56) References Cited

U.S. PATENT DOCUMENTS 5,736,823 A * 4/1998 Nordby ................ G05D 7/0676
                                                      318/432

* cited by examiner

*Primary Examiner* — Cabrena Holecek
(74) *Attorney, Agent, or Firm* — Guosheng Wang; United States Research and Patent Firm

(57) ABSTRACT

The present invention provides a ventilation system for improving air quality of an indoor space. The system includes sensors for measuring PM2.5 particle level P, $CO_2$ level C, and TVOC level T in the indoor space. A control circuit is configured to receive P, C and T values and generate an output signal Vout according to a specific algorithm, which in turn controls speed-variable EC motors that drive ventilating fans. The invention exhibits numerous technical merits such as lower energy consumption, programmable operation, high efficiency, and lower noise, among others.

20 Claims, 10 Drawing Sheets

VENTILATION SYSTEM FOR IMPROVING INDOOR AIR QUALITY, HVAC SYSTEM COMPRISING THE SAME AND PROCESS THEREOF

CROSS-REFERENCE TO RELATED APPLICATIONS

This non-provisional application expressly claims the benefit of priority under the Paris Convention based on Chinese Application No. 201610437764.6, filed on Jun. 8, 2016, the entire disclosures of which is incorporated herein by reference.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

FIELD OF THE INVENTION

The present invention generally relates to a ventilation system, a HVAC system comprising the ventilation system, and a process of using the ventilation system for improving indoor air quality. Although the invention will be illustrated, explained and exemplified using a residential building, it should be appreciated that the present invention can also be applied to other fields, for example, industrial buildings, laboratories, single family homes, apartment buildings, hotels and senior living facilities, medium to large industrial and office buildings such as skyscrapers and hospitals, onboard vessels, submarines, aircrafts, trains, universities, government facilities, semiconductor manufacturing plants, pharmaceutical manufacturing plants, chemical plants, petrochemical plants, and etcetera.

BACKGROUND OF THE INVENTION

Particulate matter (PM) is microscopic solid or liquid matter suspended in atmosphere. Larger particles are generally filtered in the nose and throat via cilia and mucus, but particulate matter smaller than about 10 micrometers can penetrate the deepest part of the lungs such as the bronchioles or alveoli, and settle in the bronchi and lungs. Finer particles with a diameter of 2.5 micrometers or less, i.e. PM2.5 particles, are deadly air pollution due to their ability to penetrate deep into the lungs and blood streams. Very small particles (<100 nanometers) such as particles emitted from modern diesel engines and soot particles may pass through the lungs to affect other organs. These nanoparticles may be damaging to the cardiovascular system, as they can pass through cell membranes and migrate into other organs, including the brain. The effects of inhaling particulate matter on the health of humans and animals include asthma, lung cancer, respiratory diseases, cardiovascular disease, permanent DNA mutations, heart attacks, premature delivery, birth defects, low birth weight, and premature death.

Volatile organic compounds (VOCs) are organic chemicals that have a high vapor pressure at ordinary room temperature. Although not acutely toxic, anthropogenic VOCs are harmful to human health in long term. Long-term exposure to volatile organic compounds (VOCs) in the indoor environment can contribute to sick building syndrome. In offices, VOC results from new furnishings, wall coverings, and office equipment such as photocopy machines, which can off-gas VOCs into the air. Leukemia and lymphoma can increase through prolonged exposure of VOCs in the indoor environment. The aromatic VOC compound benzene, emitted from exhaled cigarette smoke, is labeled as carcinogenic and is ten times higher in smokers than in nonsmokers. EPA has found concentrations of VOCs in indoor air to be 2 to 5 times greater than in outdoor air. Studies have shown that individual VOC emissions by themselves are not that high in an indoor environment, but the indoor total VOC (TVOC) concentrations can be up to five times higher than the VOC outdoor levels.

Ozone is another air contaminant. Combustion of fossil fuels can emit pollutants as ozone precursors, which, when irradiated by UV rays, produce tropospheric ozone near the Earth's surface. In China, fossil fuel burning raises ground level ozone far above background levels. Ground-level ozone may harm lung function and irritate the respiratory system. Exposure to ozone and its precursor is linked to premature death, asthma, bronchitis, heart attack, and other cardiopulmonary problems. Long-term exposure to ozone may increase risk of death from respiratory illness. Ozone can also be present in indoor air pollution, partly as a result of electronic equipment such as photocopiers. Because of the strongly oxidizing properties of ozone, ozone is a primary irritant, affecting especially the eyes and respiratory systems and can be hazardous at even low concentrations. When inhaled, ozone reacts with compounds lining the lungs to form specific, cholesterol-derived metabolites that are thought to facilitate the build-up and pathogenesis of atherosclerotic plaques, a form of heart disease.

$CO_2$ per se is not an air contaminant, but it can indirectly reflect the level of indoor oxygen level. As a rule of thumb, the higher the indoor $CO_2$ level, the lower the indoor oxygen level. CO2 is typically found in outside air at concentrations between 300 and 500 PPM and is exhaled by human beings at an approximate rate of 0.01 CFM per person for a person doing typical office work. Variations in the number of people in an office compared to the amount of outside air supplied into the building can easily increase indoor CO2 levels to between 500 and 2500 PPM. As such, CO2 can be used as an excellent indicator of proper ventilation on a per person basis sometimes referred to as the CFM of outside air per person since the level of CO2 in a space is directly related to the number of people in a space divided by the rise in CO2 from outdoor levels. Human beings are unaffected by relatively high levels of CO2 such as up to 5000 PPM, which would be extremely rare to find in any building of ordinary construction. However, inadequate oxygen supply may cause generalized hypoxia, the symptoms associated with which range from fatigue, numbness, tingling of extremities, to nausea and anoxia. In severe hypoxia, or hypoxia of very rapid onset, ataxia, confusion, disorientation, hallucinations, behavioral change, severe headaches, and reduced level of consciousness may be the symptoms.

Today, people spend 90% of their time indoors, and indoor air quality/comfort is essential for the occupants' well-being. Accurate monitoring the indoor levels of PM2.5 particles, $CO_2$ and TVOC, followed by "smart" and efficient ventilating of the indoor space, is no doubt the most important goal of many industrial researches and developments.

Advantageously, the present invention provides a ventilation system, a HVAC system comprising the ventilation system, and a process of using the ventilation system for improving air quality, that can meet the need as described above.

SUMMARY OF THE INVENTION

One aspect of the present invention provides a ventilation system for improving air quality of an indoor space. The system includes a PM2.5 particle sensor for measuring PM2.5 particle level P in the indoor space; a $CO_2$ sensor for measuring $CO_2$ level C in the indoor space, a TVOC sensor for measuring TVOC level T in the indoor space; a first motor driving a first air blower for introducing an outdoor air stream into the indoor space; and a control circuit configured to receive the values of P, C and T from the three sensors, and to generate an output signal Vout according to the equation of Vout=$(a \times P + b \times C + c \times T)/d$, $a>0$, $b>0$, $c>0$, and $d \neq 0$. The output signal Vout is used to continuously vary the first motor's speed or torque.

Another aspect of the invention provides a HVAC system comprising the ventilation system as described above.

A further aspect of the invention provides a process for improving air quality of an indoor space, comprising:

measuring PM2.5 particle level P in the indoor space using a PM2.5 particle sensor;

measuring $CO_2$ level C in the indoor space using a $CO_2$ sensor;

measuring TVOC level. T in the indoor space using a TVOC sensor;

introducing an outdoor air stream into the indoor space using a first motor driving a first air blower;

generating, after a control circuit receives the values of P, C and T from the three sensors, an output signal Vout by the control circuit according to the equation of Vout=$(a \times P + b \times C + c \times T)/d$, wherein $a>0$, $b>0$, $c>0$, and $d \neq 0$; and varying the first motor's speed or torque using the output signal Vout.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying, drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

Figure 1:
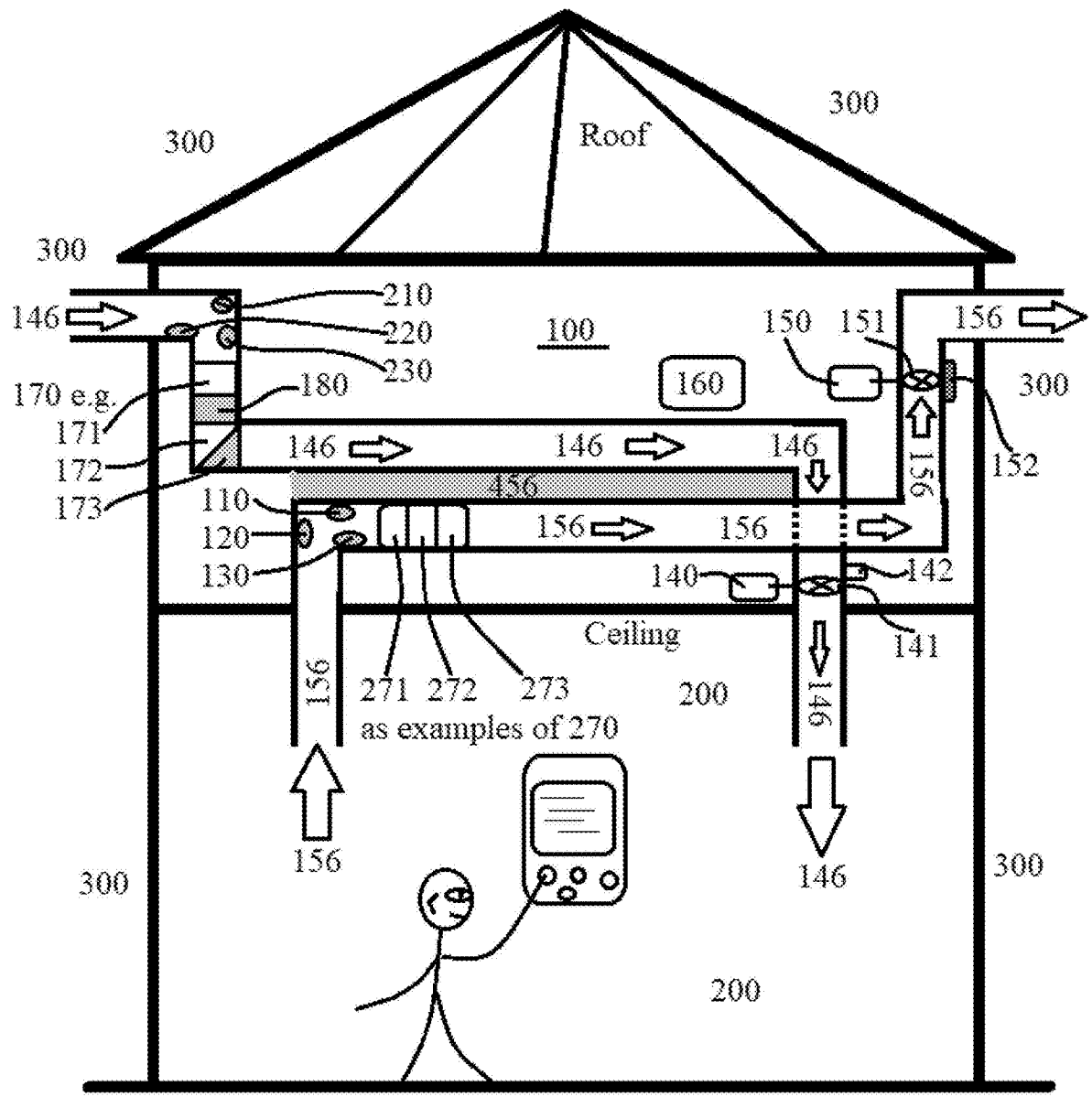
FIG. 1 schematically shows a ventilation system in a residential building in accordance with an exemplary embodiment of the present invention.

Referring to FIG. 1, an exemplary residential building includes a roof, a ceiling, and an indoor space 200. Installed between the ceiling and the roof is a ventilation system 100 for ventilating air from outdoor 300 to indoor space 200, and therefore improving the air quality therein. Ventilation system 100 includes three sensors: a PM2.5 particle sensor 110 for measuring PM2.5 particle level P in the indoor space 200, a $CO_2$ sensor 120 for measuring $CO_2$ level C in the indoor space 200, and a TVOC sensor 130 for measuring TVOC level T in the indoor space 200. PM2.5 particle sensor 110 may be operated using an optical method, in a manner similar to, for example, a standard laser air quality monitor. In an embodiment, PM2.5 particle sensor 110 is laser based air quality sensor such as PMS 1003 sensor commercially available from Plantower Inc (Beijing, China) The carbon dioxide sensor 120 may be any suitable sensor. For example, it can be a spectroscopic sensor such as nondispersive infrared gas sensor (NDIR), which detects CO2 in a gaseous environment by its characteristic absorption. A NDIR sensor includes an infrared source, a light tube, an interference (wavelength) filter, and an infrared detector. CO2 is pumped or diffuses into the light tube, and then the electronics measures the absorption of the characteristic wavelength of light. Sensor 120 may be a chemical CO2 gas sensors with sensitive layers based on polymer- or heteropolysiloxane. In an embodiment, Sensor 120 is S8 0013 sensor commercially available from SenseAir, Sweden. TVOC sensor 130 may be a MEMS metal oxide sensor, commercially available from e.g. CCS (Cambridge CMOS Sensors). TVOC sensor 130 may be protected by a plastic cap and a filter membrane. The sensor module can be soldered directly to a host circuit board with selective or reflow soldering via the edge connectors.

Referring again to FIG. 1, a first motor 140 drives a first air blower 141 for introducing an outdoor subaerial air stream 146 into the indoor space 200. Air stream 146 may be used for diluting and/or displacing indoor pollutants. If it is for displacing indoor pollutants, a second motor 150 drives a second air blower 151 is preferably used for discharging an indoor air stream 156 from the indoor space 200 to outdoor 300. In addition to reduce PM2.5 particles and ozone, ventilation system 100 can also provide additional benefits such as temperature control, oxygen replenishment, and removal of moisture, unpleasant smells and odors, heat, airborne bacteria, carbon dioxide, and other gases. Ventilation system 100 keeps interior air circulating, and prevents stagnation of the interior air.

In various embodiments, both motors are electronic commutation (EC) motors, AKA brushless DC electric motor (BLDC motors, BL motors). The EC motors utilize an electronic circuit board to control the functionality of the motor. The motor may operate off of 115V or 220V AC single phase power, which is converted to DC power within the motor's circuitry. A control lead may be prewired from the motor which accepts a 0-10V DC signal (Vout) Control circuit 160 can slow down or speed up electric motor 140/150 to meet changing indoor climate demands or requirements. Varying the speed of fan and associated electric motor 140/150 can improve process control to meet changing speed or torque demands on a motor-driven system, can reduce ambient noise levels in occupied spaces as measured in decibels; and can reduce energy consumption as measured in kilowatt-hours (kWh) of electricity. Other benefits include fossil fuel savings, improved safety, increased productivity, and decreased occupant illness. In an embodiment, motors 140 and 150 are R3G 140 AV 03-02 EC centrifugal fans commercially available from ebm-papst Mulfingen GmbH & Co KG, Germany.

A control circuit 160 is configured to receive the values of P, C and T from the three sensors 120, 130 and 140. Then circuit 160 is configured to calculate or generate an output signal Vout according to the equation of Vout=(a×P+b×C+c×T)/d, in which a>0, b>0, c>0, and d≠0. Signal Vout is used to vary continuously one or two of said two motors' (140 and 150) speed or torque. Different Vout values will control the motor or motors rotate at different speeds or torques. In various embodiments, PM2.5 particle level P is in unit of $\mu g/m^3$, $CO_2$ level C is in unit of ppm, TVOC level T is in unit of ppb, Vout is in unit of mV, 8<a<25, 0.8<b<2, 0.8<c<2, and d=400. Generally, Vout is in (or is truncated to be in) the range of 0-10V, or more precisely, 0<Vout<10000 (mV).

Control circuit 160 may be adapted to operate in accordance with an algorithm that controls or at least partially controls one or more components of system 100. A user interface may be any suitable interface that permits control circuit 160 to display and/or solicit information as well as permitting a user to enter data. In some cases, the user interface may include a display and a distinct keypad A display may be any suitable alphanumeric display. In some instances, a display may include or may be a liquid crystal display (LCD) if desired, the user interface may be a touch screen LCD panel that functions as both display and keypad. In some instances, a touch screen LCD panel may be adapted to solicit values for a number of operating parameters and/or to receive said values.

Control circuit 160 may include a memory block to store any desired information, such as the aforementioned control algorithm/equation. Control circuit 160 may store information within memory block and may subsequently retrieve the stored information. The memory block may be any suitable type of storage device, such as RAM, ROM, EPROM, a flash drive, a hard drive, and the like.

Control circuit 160 may include a data port. The data port may be a wireless port such as a Bluetooth port or any other wireless protocol. In some cases, the data port may be a wired port such as a serial port, a parallel port, a CAT5 port, a USB (universal serial bus) port, or the like. In some instances, the data port may be a USB port and may be used to download and/or upload information from a USB flash drive. Other storage devices may also be employed, as desired.

If outdoor air is polluted with PM2.5 particles, ventilation system 100 may further include one or more filters 170 for reducing PM2.5 particle level in an outdoor air stream 146 that is to be introduced into the indoor space 200. For example, filters 170 may include an initial-efficiency filter 171, an intermediate-efficiency filter 172, and a high-efficiency filter 173 arranged consecutively from upstream to downstream along flow direction of said outdoor air stream 146 that is to be introduced into the indoor space.

Figure 7:
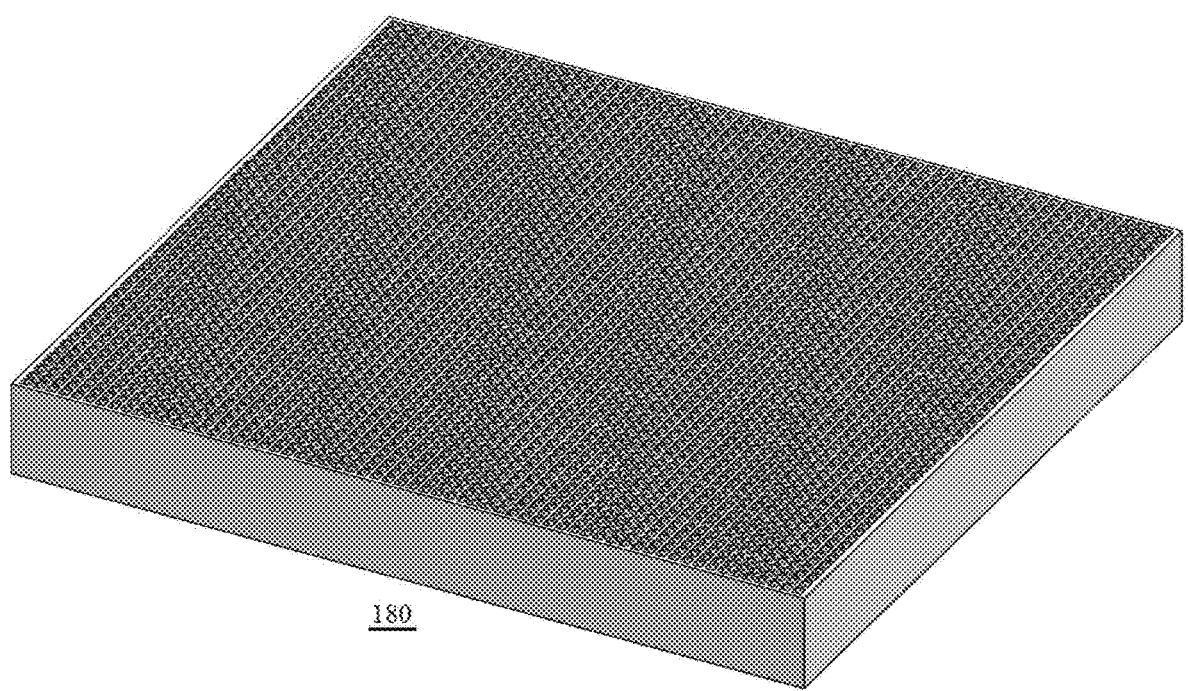
FIG. 7 shows an ozone filter used in a ventilation system in accordance with an exemplary embodiment of the present invention.

If outdoor air is polluted with ozone, ventilation system 100 may further include an ozone filter 180 for reducing ozone level in an outdoor air stream 146 that is to be introduced into the indoor space 200. Ozone filter 180 may be placed in any suitable position along the air stream. In FIG. 1, ozone filter 180 is placed between the initial-efficiency filter 171 and the intermediate-efficiency filter 172. In a preferred embodiment as shown in FIG. 7, ozone filter 180 is made from cordierite honeycomb ceramic material loaded with a catalyst, such as $CuMn/CeO_2$—Al2O3 catalyst. Such an ozone filter may be square shaped, and may have a thickness of 20 mm.

In preferred embodiment, the noise generated from the motors and blowers are properly treated, and the quietness of indoor space 200 is not disturbed. For example, ventilation system 100 may further include a first active noise reduction (ANR) module 142 for canceling noise generated from said first air blower 141 through destructive interference. A second active noise reduction (ANR) module 152 may also be used for canceling noise generated from said second air blower 151 through destructive interference.

In preferred embodiment, ventilation system 100 is energy efficient and environmentally friendly. For example, outdoor air stream 146 and indoor air stream 156 may be so configured that complete, or as much as possible, exchange heat can be carried out through an airtight membrane 456 between them. It should be appreciated that the present invention can use any suitable heat recovery ventilation (i-IRV) equipment, heat recovery ventilator, heat exchanger, air exchanger, air-to-air heat exchanger which employs a cross flow or counter-flow heat exchanger (countercurrent heat exchange) between the inbound and outbound air flow, and/or energy recovery ventilators (ERs) capable of transferring the humidity level of the exhaust air to the intake air. Examples of air-to-air heat exchangers include, but are not limited to, cross flow heat exchanger, recuperator or cross plate heat exchanger, thermal wheel or rotary heat exchanger, heat pipe, thin multiple heat wires or fine wire heat exchanger, shell and tube heat exchanger, plate heat exchanger, plate fin heat exchanger, ground-coupled heat exchanger, dynamic scraped surface heat exchanger, waste heat recovery unit, micro heat exchanger, and moving bed heat exchanger.

One or more filters 270 may be employed for reducing PM2.5 particle level in indoor air stream 156 that is to be discharged into the environment, i.e. outdoor 300. For example, filters 270 may include an initial-efficiency filter 271, an intermediate-efficiency filter 272, and a high-efficiency filter 273 arranged consecutively from upstream to downstream along flow direction of indoor air stream 156 that is to be discharged into outdoor 300, for reducing PM2.5 particle level in said indoor air stream 156.

In exemplary embodiments, ventilation system 100 includes 3 more sensors for monitoring outdoor air quality. These sensors may be a PM2.5 particle sensor 210 for measuring PM2.5 particle level P in outdoor 300, a $CO_2$ sensor 220 for measuring $CO_2$ level C in outdoor 300, and a TVOC sensor 230 for measuring TVOC level T in outdoor 300. As known to a skilled person in the art, real-time comparison between PM2.5 particle level P and TVOC level T in outdoor 300 and those in indoor space helps the maintenance of the filters, for example, the comparison data can be used to estimate whether or not the filters are saturated, and need to be replaced.

Figure 2:
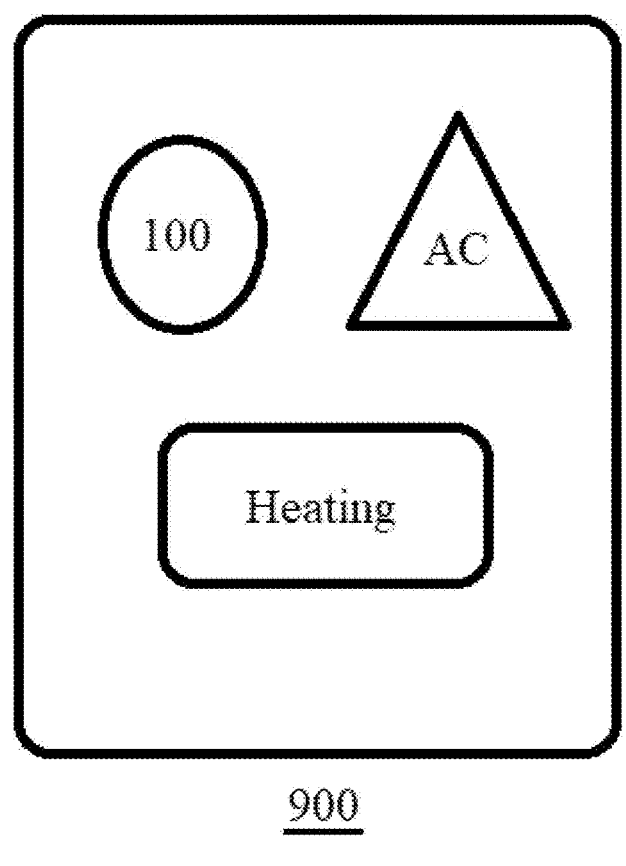
FIG. 2 schematically illustrates a HVAC system in accordance with an exemplary embodiment of the present invention.

Ventilation system 100 as described above may be incorporated into a general HVAC system 900, as shown in FIG. 2. Heating, ventilation, and/or air conditioning (HVAC) systems are often used to control the comfort level within a building or other structure. Many HVAC controllers include a controller that activates and deactivates one or more HVAC components of the HVAC system to affect and control one or more environmental conditions within the building. These environmental conditions can include, but are not limited to, temperature, humidity, and/or ventilation. In many cases, such HVAC controller may include, or have access to, one or more sensors, and may use parameters provided by the one or more sensors to control the one or more HVAC components to achieve desired programmed or set environmental conditions. The details of general HVAC are known in the art, and will not be described here for conciseness.

The present invention also provides a process for improving air quality of an indoor space 200 using ventilation system 100. The process includes the following steps: (i) measuring PM2.5 particle level P in the indoor space using a PM2.5 particle sensor; (ii) measuring $CO_2$ level C in the indoor space using a $CO_2$ sensor; (iii) measuring TVOC level T in the indoor space using a TVOC sensor; (iv) introducing an outdoor air stream into the indoor space using a first motor driving a first air blower; (v) generating an output signal Vout according to the equation of Vout=(a×P+b×C+c×T)/d, a>0, b>0, c>0, and d≠0 by a control circuit, after the control circuit receives the values of P, C and T from the three sensors; and (vi) varying one or two of said two motors' speed or torque using the output signal Vout. In various embodiments, PM2.5 particle level P is in unit of $\mu g/m^3$, $CO_2$ level C is in unit of ppm, TVOC level T is in unit of ppb, Vout is in unit of mV, 8<a<25, 0.8<b<2, 0.8<c<2, and d=400. The process may further comprise two additional steps: discharging an indoor air stream from the indoor space to outdoor using a second motor driving a second air blower; and varying the second motor's speed or torque using the output signal Vout.

The process may further comprise two additional steps: (iv-a) providing one or more particle filters; and (iv-b) reducing PM2.5 particle level in an outdoor air stream that is to be introduced into the indoor space with said one or more particle filters.

The process may further comprise two additional steps: (iv-1) providing an ozone filter, and (iv-2) reducing ozone level in an outdoor air stream that is to be introduced into the indoor space using the ozone filter.

The process may further comprise two additional steps: (45-*a*) providing a first active noise reduction (ANR) module; and (45-*b*) canceling noise generated from said first air blower through destructive interference with said first active noise reduction (ANR) module.

The process may further comprise two additional steps: (45-1) providing a second active noise reduction (ANR) module; and (45-2) canceling noise generated from said second air blower through destructive interference with said second active noise reduction (ANR) module.

Figure 3:
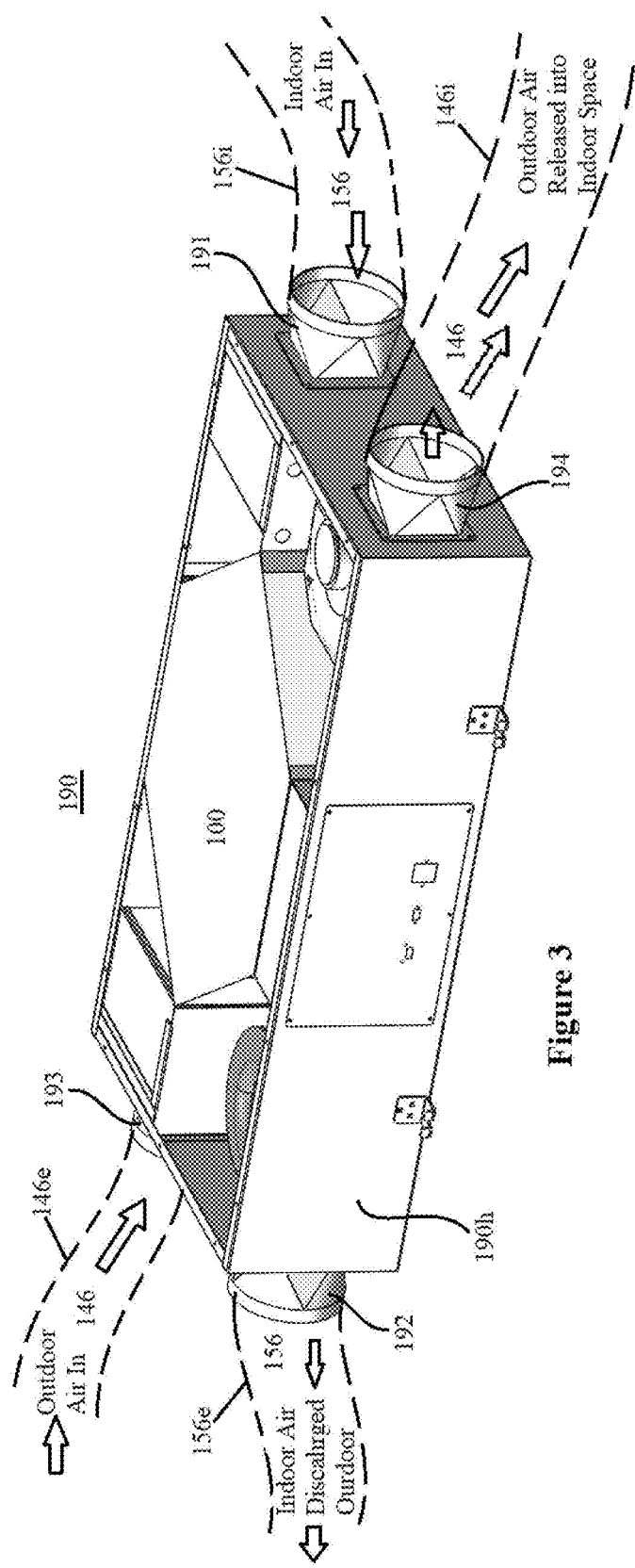
FIG. 3 illustrates a single-unit ventilation system in accordance with an exemplary embodiment of the present invention.

Referring to FIG. 3, components of ventilation system 100 may be manufactured and assembled into a single unit 190 with a housing 190*h*, which is shipped to customers for installation. Single unit 190 may have four air duct interfaces 191, 192, 193 and 194, for connecting to air ducts 156*i*, 156*e*, 146*e* and 146*i*, respectively. Air stream 146 is sucked into air duct 146*e* from outdoor environment 300, passes through interface 193, enters system 100 for treatment, exits from system 100 through interface 194 into air duct 146*i*, and finally releases into indoor space 200. Air stream 156 is sucked into air duct 156*i* from indoor space 200, passes through interface 191, enters system 100 (where air treatment is optional), exits from system 100 through interface 192 into air duct 156*e*, and finally releases into outdoor environment 300.

Figure 4:
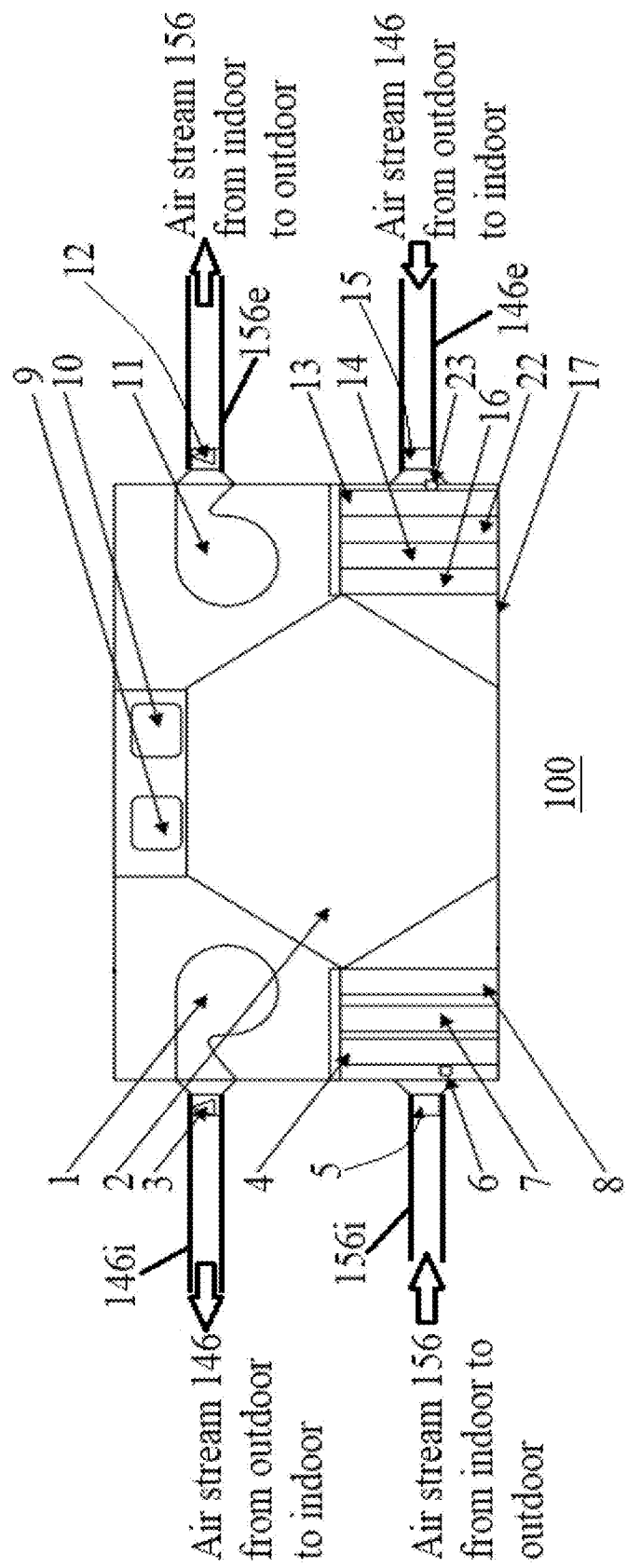
FIG. 4 demonstrates a specific ventilation system in a residential building in accordance with an exemplary embodiment of the present invention.

In an embodiment, unit 190 may include eight modules, i.e. a fan module, a total heat exchange module, a filter module, a sensor control module, a remote monitor module, an active noise reduction module, a casing module, and an ozone-decomposing module. Referring to FIG. 4, the fan module includes outlet fan 1 driving air stream 146 through system 100, and exhaust fan 11 driving air stream 156 through system 100. The total heat exchange module includes a total heat exchange film 2. The filter module includes a return air filters set and an inlet air filters set. In the return air filters set, return air primary-effect filter 4, return air middle-effect filter 7 and return air high-effect filter 8 may be properly combined depending on the conditions. The inlet air filters set may include inlet air primary-effect filter 13 inlet air middle-effect filter 14, and inlet air high-effect filter 16. The sensor control module includes indoor sensor combination board 6, outdoor sensor combination board 23 and central control board 9.

Figure 5:
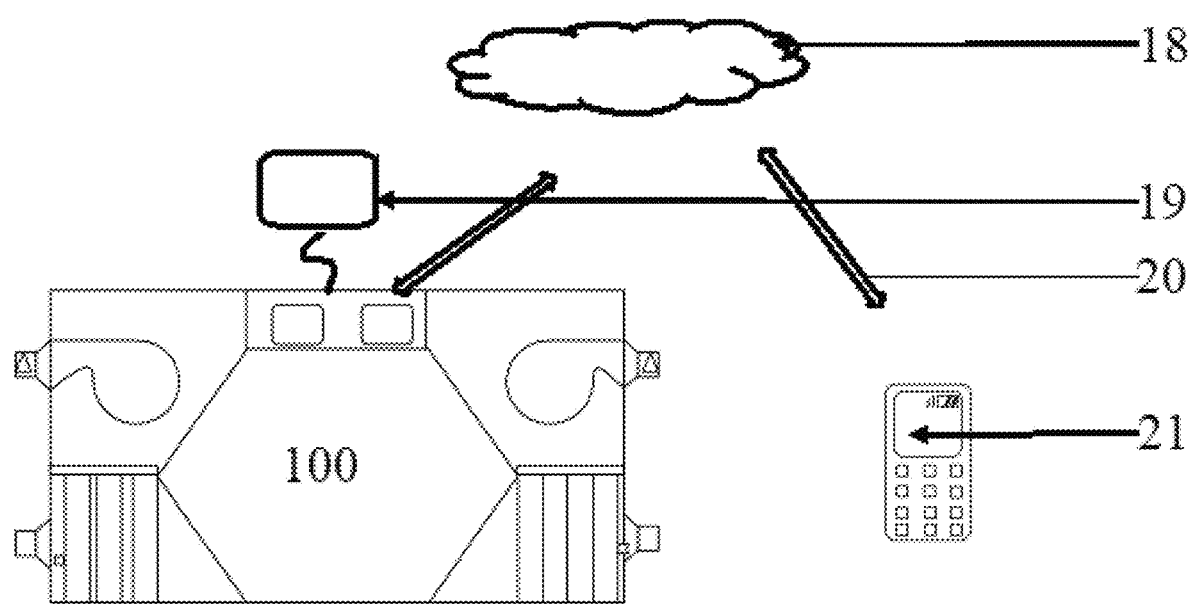
FIG. 5 depicts a ventilation system with a remote monitor module in accordance with an exemplary embodiment of the present invention.

As shown in FIG. 4 and FIG. 5, the remote monitor module includes remote monitor board 10, back stage cloud 18, wireless data communication link 20, and user mobile terminal 21.

Referring back to FIG. 4, the active noise reduction module includes air outlet noise-reduction structure 3 and exhaust port noise-reduction structure 12. The casing module includes air outlet 5, fresh air port 15, and equipment casing 17. The ozone-decomposing module 22 is installed next to inlet air primary-effect filter 13 of the inlet air filters set, for example between filter 13 and filter 14. Module 22 is a cellular module made of a ceramic material capable of decomposing ozone at normal temperature.

Figure 6:
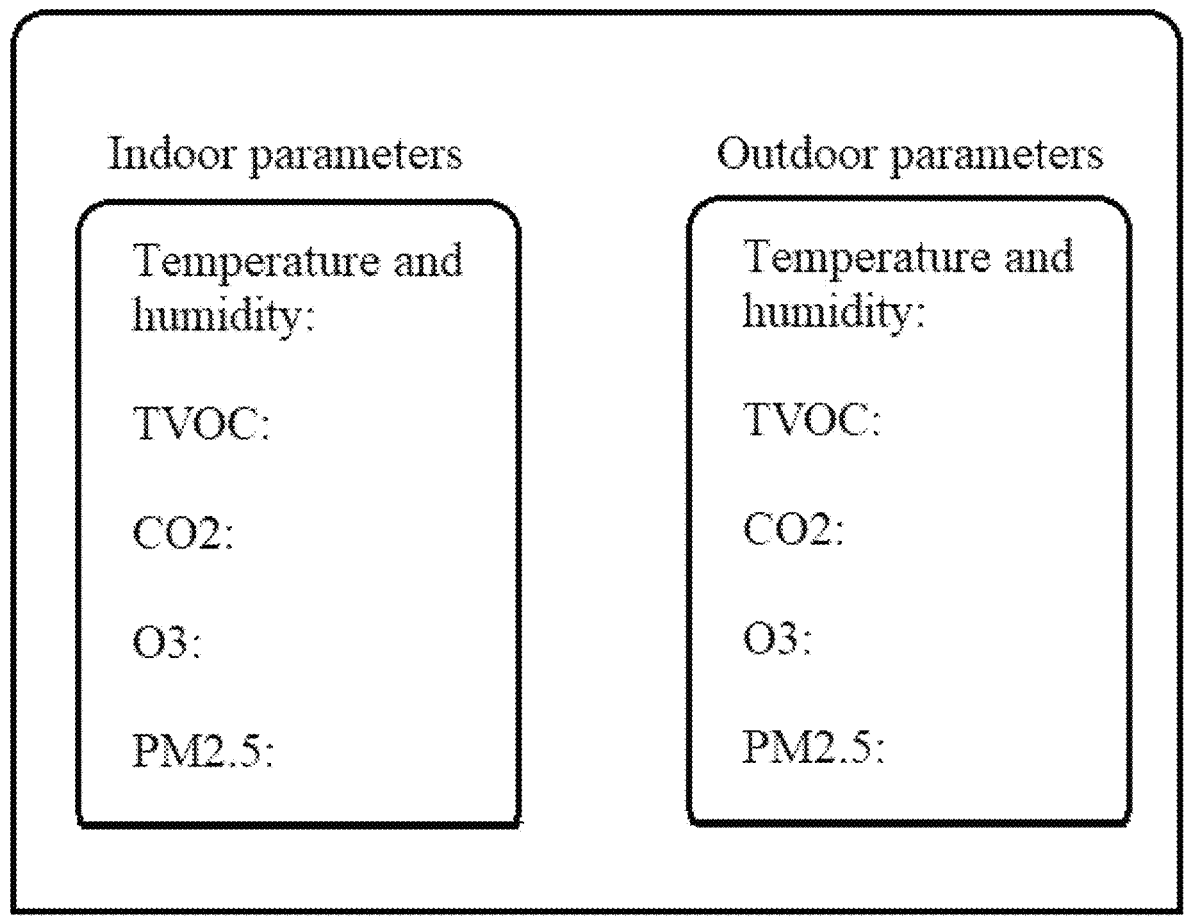
FIG. 6 schematically shows a display panel used in a ventilation system in accordance with an exemplary embodiment of the present invention.

Air outlet noise-reduction structure 3 and exhaust port noise-reduction structure 12 are fixed at the air outlet of outlet fan 1 and exhaust fan 11, respectively. The indoor air sensor combination board 6 is fixed upstream relative to return air primary-effect filter 4. Sensors on board 6 may include a TVOC sensor, a $CO_2$ sensor, a laser particles sensor, a temperature-humidity sensor, and an ozone concentration sensor Outdoor sensor combination board 23 is fixed after fresh air inlet 15 and before air primary-effect filter 13. Sensors on board 23 may include a TVOC sensor, a $CO_2$ sensor, a laser particles sensor, a temperature-humidity sensor, and an ozone concentration sensor. The fans 1 and 11 in the fan module are EC adjustable fans. Total heat exchange module 2 employs a total heat & moisture polymeric exchanger with an efficiency of up to 92% Ozone-decomposing module 22 is fixed after the inlet air primary-effect filter 13 of the inlet air filters set, which is a cellular module based on ceramic material, or a plasma module, for decomposing ozone at normal temperature. The indoor and outdoor ozone sensor signal from boards 6 and 23 may be transmitted to a display panel 600 as shown in FIG. 6. A user can view the indoor and outdoor ozone concentrations, and evaluate the status of the ozone-decomposing module.

Figure 8:
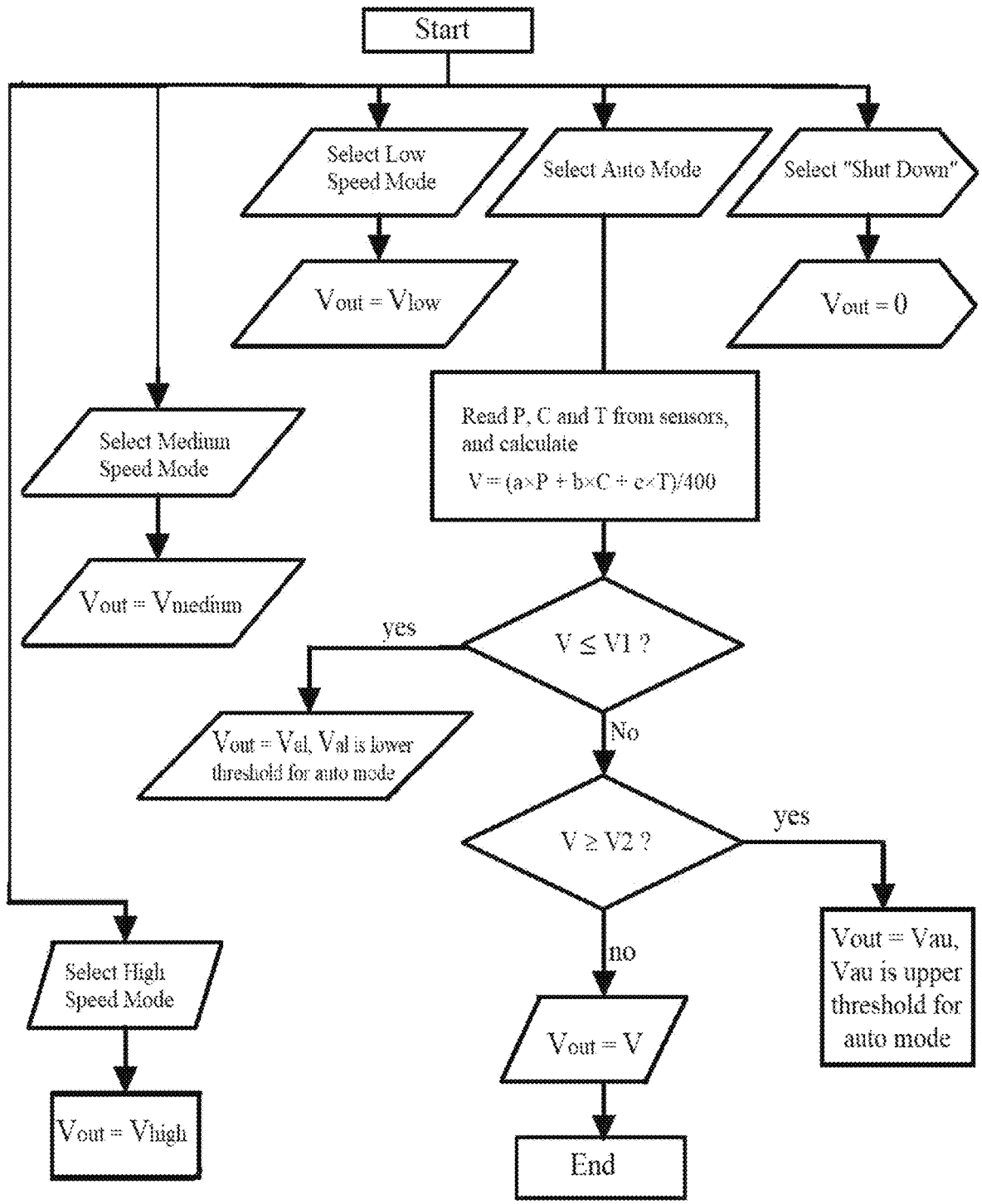
FIG. 8 schematically shows a process of using, a ventilation system according to an embodiment of the present invention.

FIG. 8 illustrates a process of using the ventilation system 100 for improving, air quality of an indoor space 200 according to an embodiment of the present invention. Referring to FIG. 8, the process starts by manually selecting one mode option out of five mode options, including "low speed", "medium speed", "high speed", "auto speed" and "shut down" In the "low speed" mode, Vout from control circuit 160 is configured to set at a predetermined and constant low value Vlow, and two motors 140/150 are configured to run at a low speed. In the "medium speed" mode, Vout from control circuit 160 is configured to set at a predetermined and constant medium value Vmedium>Vlow, and two motors 140/150 are configured to run at a medium speed that is faster than the low speed. In the "high speed" mode, Vout from control circuit 160 is configured to set at a predetermined and constant high value Vhigh>Vmedium, and two motors 140/150 are configured to run at a high speed that is faster than the medium speed. In the "shut down" mode, Vout from control circuit 160 is configured to set at 0, and two motors 140/150 are configured to stop running.

In the "auto speed" mode, control circuit 160 is configured to read P, C and T from corresponding sensors as described above Control circuit 160 is then configured to calculate V according to the formula: $V=(a \times P + b \times C + c \times T)/400$. If $V \leq V1$, then Vout is set as Val, wherein Val is a lower threshold for auto mode, and V1 and Val may be the same or different from each other. If V>V1, then V is compared to V2. If $V \geq V2$, then Vout is set as Vau, wherein Vau is an upper threshold for auto mode, and V2 and Vau may be the same or different from each other. If V<V2, then Vout is set as V, which is variable in real time as P, C and T are varying.

In typical embodiments, Vlow, Vmedium and Vhigh are independently of each other within the range of 0~10000 mV The values of V1, V2, Val and Vau may be manually set, and typically each of them is independently of each other within the range of 0~10000 mV as well. PM2.5 particle level P may be an average of ten signals (P1, P2, . . . P10) measured in 1 second by a PM2.5 particle sensor. If one of the ten signals exceeds a predetermined range, that signal will be treated as an error reading, and removed from the calculation. The next signal may be used to replace the removed signal. Similarly, $CO_2$ level C may be an average of ten signals (C1, C2, . . . C10) measured in 1 second by a $CO_2$ sensor. If one of the ten signals exceeds a predetermined range, that signal will be treated as an error reading, and removed from the calculation. The next signal may be used to replace the removed signal. Similarly, TVOC level T may be an average of ten signals (T1, T2, . . . T10) measured in 1 second by a TVOC sensor. If one of the ten signals exceeds a predetermined range, that signal will be treated as an error reading, and removed from the calculation. The next signal may be used to replace the removed signal.

Figure 9:
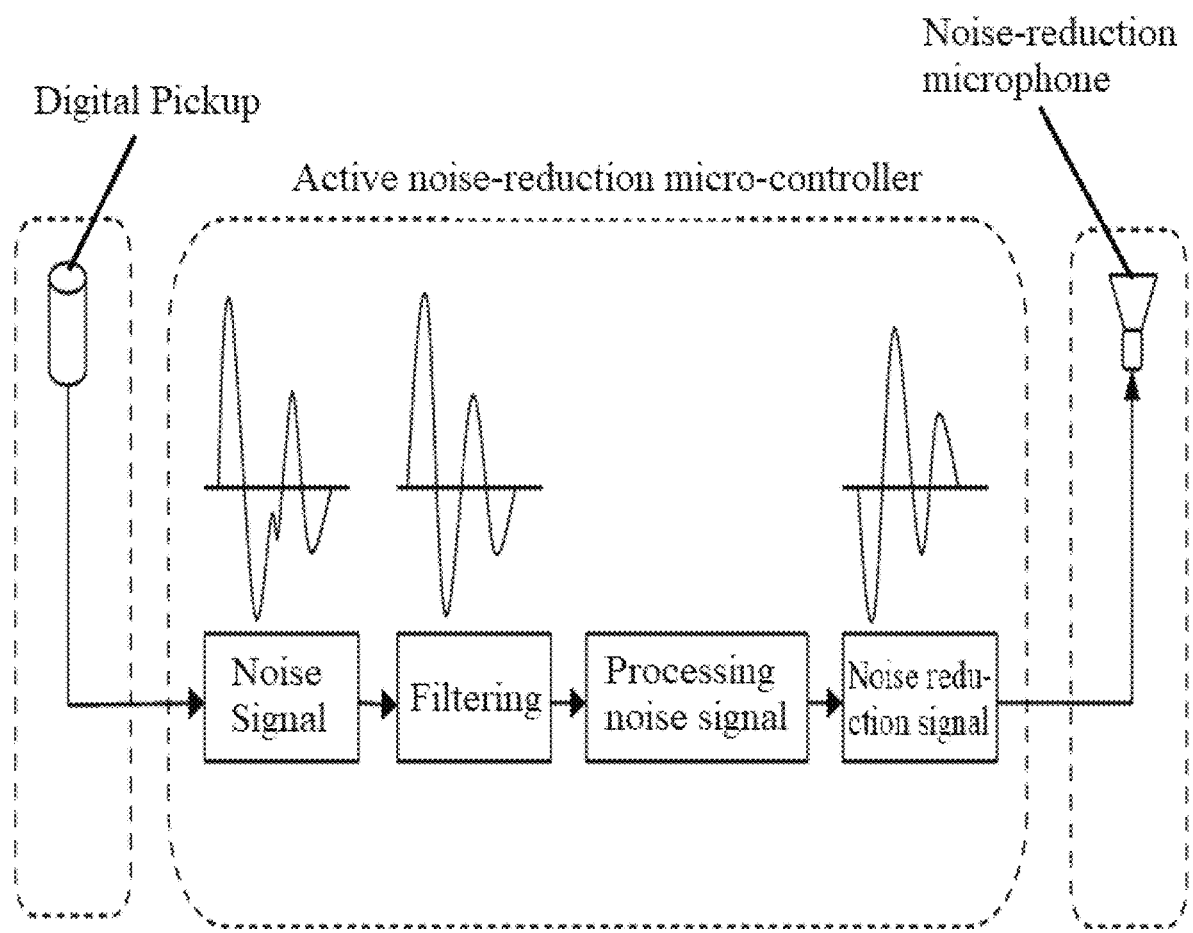
FIG. 9 schematically shows noise-reduction structure used in a ventilation system in accordance with an exemplary embodiment of the present invention.

Referring back to FIG. 4 and the description thereof in the above, when the ventilation system 100 is started, both fan 1 and fan 11 may by default enter the low-speed mode, and the indoor sensor module 6 starts to work, and on real-time transmits values of TVOC, $CO_2$, temperature, humidity and particle concentration acquired at air outlet 5 to the central control board 9. After processing of the acquired data using the algorithm as described above, central control board 9 outputs the control signal to both outlet fan 1 and exhaust fan 11, and the both fans run at corresponding speed depending on the received control signal so as to automatically adjust the air flow rate as per the concentration of the contaminants in the air. At same time, the outdoor fresh air from the air inlet 15 enters the total heat exchange module through the inlet air primary-effect filter, ozone-decomposing module, inlet air middle-effect filter and inlet air high-effect filter. In the total heat exchange module, the fresh air conducts heat-humidity exchange with the exiting indoor air which enters the total heat exchange module from air outlet 5 through the return air filters set. The outdoor fresh air through the outlet fan 1 is fed to the indoor, and indoor air is discharged outdoors through the exhaust fan 11, thereby the function of supplying fresh air from the outdoor to the indoor is realized. After ventilation system 100 is started, the active noise reduction module will autonomously start to work. The air outlet noise-reduction structure 3 and the exhaust port noise-reduction structure 12 of the active noise reduction module are similar or the same; and they work in a similar/same manner as well. After system 100 is energized, structures 3 and 12 simultaneously start to work. As shown in FIG. 9, the air outlet noise-reduction structure 3 may include a digital pickup, a micro-processor, and a noise-reduction microphone. The digital pickup first acquires the environmental noise at the air outlet, transforms the noise from analog signal to digital signal, and transmits the digital signal to the micro-controller. The micro-controller filters the digital signal, and then processes the filtered signal. Next, the micro-controller generates noise-reduction waves with amplitude same as, but phase reversed to, the noise signal. The micro-processor transmits noise-reduction waves to a noise-reduction microphone. Finally, the noise-reduction microphone emits the noise-reduction waves, accomplishing reverse-phase elimination and neutralization of the noise signal.

Figure 10:
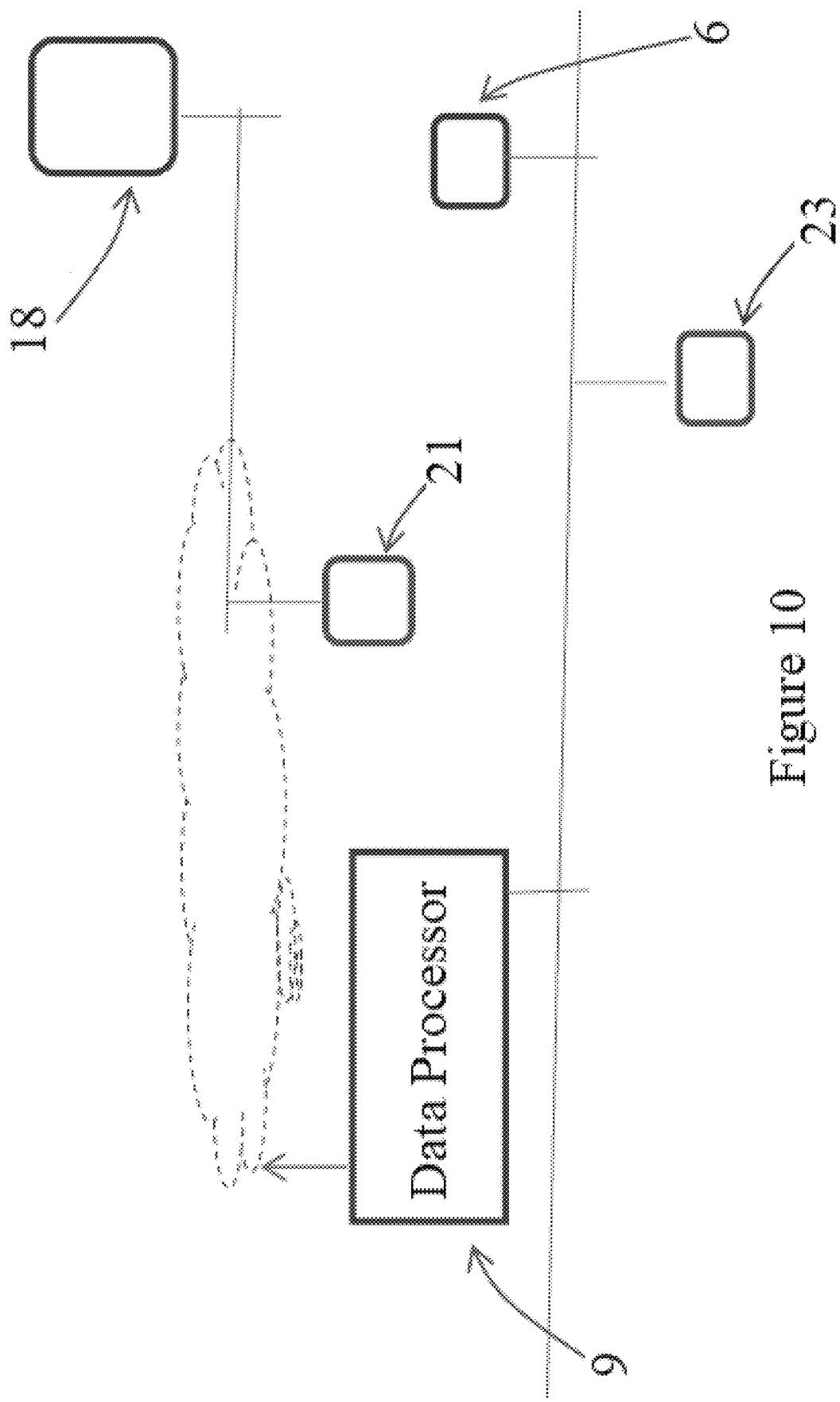
FIG. 10 depicts a ventilation system with a remote monitor module in accordance with an exemplary embodiment of the present invention.

In another embodiment, when the ventilation system 100 is started, both fan 1 and fan 11 may by default enter the low-speed mode, and the indoor sensor module 6 starts to work, and on real-time transmits values of TVOC, $CO_2$, temperature, humidity and particle concentration acquired at air outlet 5 to the central control board 9. After processing of the acquired data using the algorithm as described above, central control board 9 outputs the control signal to both outlet fan 1 and exhaust fan 11, and the both fans run at corresponding speed depending on the received control signal so as to automatically adjust the air flow rate as per the concentration of the contaminants in the air. As shown in FIG. 10, the outdoor air quality information acquired by the outdoor sensor combination board 23 is displayed on a user mobile terminal such as a local touch panel 21. The central control board 9 transmits the data received from the sensors in package to the remote monitor module. The remote monitor module transmits the data to the back stage cloud 18 through the wireless data communication link 20. The back stage cloud 18 transmits the corresponding data to the user mobile terminal 21 for display through the wireless data communication link 20. At that time, the outdoor fresh air 146 from the air inlet enters the total heat exchange module through the inlet air primary-effect filter, ozone-decomposing module, inlet air middle-effect filter and inlet air high-effect filter and is then fed to the indoor through the outlet fan 1. In the total heat exchange module, the fresh air conducts heat-humidity exchange with the exiting indoor air which enters the total heat exchange module from the return air-port 5 through return air filter. The exiting indoor air is discharged outdoors through the exhaust fan 11. When the central control board 9 receives the constant fan speed instruction from a local input equipment 19, or receives the instruction transmitted from the remote user mobile terminal 21 through the remote monitor module, the central control board 9 outputs the control signal to the both fans 1 and 11 as per the constant speed instruction, and both fans run at specified speed as per the control signal. When the central control board 9 receives an on/off instruction from the local input equipment 19, or through the remote monitor module, system is turned on/off. After ventilation system 100 is started, the active noise reduction module will autonomously start to work. The air outlet noise-reduction structure 3 and the exhaust port noise-reduction structure 12 of the active noise reduction module are similar or the same, and they work in a similar/same manner as well. After system 100 is energized, structures 3 and 12 simultaneously start to work. As shown in FIG. 9, the air outlet noise-reduction structure 3 may include a digital pickup, a micro-processor, and a noise-reduction microphone. The digital pickup first acquires the environmental noise at the air outlet, transforms the noise from analog signal to digital signal, and transmits the digital signal to the micro-controller. The micro-controller filters the digital signal, and then processes the filtered signal. Next, the micro-controller generates noise-reduction waves with amplitude same as, but phase reversed to, the noise signal. The micro-processor transmits noise-reduction waves to a noise-reduction microphone. Finally, the noise-reduction microphone emits the noise-reduction waves, accomplishing reverse-phase elimination and neutralization of the noise signal.

The present invention exhibits numerous technical merits. For example, fresh air fans in the prior art are usually AC fans, which consumes more power and makes bigger noise, and are unsuitable for households application. This invention uses speed-variable fresh air fans or blowers. The total heat exchange module employs an ultra-thin polymer film that increases the heat-moisture exchange efficiency up to 92%. As EC speed-variable fan is used, maximum power usage is controlled and dropped down to 60 W, and, as a result, the noise is lowered as well. Due to excessively high outdoor PM2.5 level, the system adopts three stages (primary-, middle- and high-effect) filtering. The high-effect filter is manufactured with static spinning technology to meet the requirements of the indoor air quality.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, processor-executed, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or executable instructions that, when executed by one or more processor devices, cause the host computing system to perform the various tasks. In certain embodiments, the program or code segments are stored in a tangible processor-readable medium, which may include any medium that can store or transfer information. Examples of suitable forms of non-transitory and processor-readable media include an electronic circuit, a semiconductor memory device, a ROM, a flash memory, an erasable ROM (EROM), a floppy diskette, a CD-ROM, an optical disk, a hard disk, or the like.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A ventilation system for improving air quality of an indoor space, comprising
 a PM2.5 particle sensor for measuring PM2.5 particle level P in the indoor space,
 a $CO_2$ sensor for measuring $CO_2$ level C in the indoor space;
 a TVOC sensor for measuring TVOC level T in the indoor space;
 a first motor driving a first air blower for introducing an outdoor air stream into the indoor space; and
 a control circuit configured to receive the values of P, C and T from the three sensors, and to generate an output signal Vout according to the equation of $Vout = (a \times P + b \times C + c \times T)/d$, $a > 0$, $b > 0$, $c > 0$, and $d \neq 0$;
 wherein the output signal Vout is used to vary the first motor's speed or torque.

2. The ventilation system according to claim 1, wherein said PM2.5 particle level P is in unit of $\mu g/m^3$, said $CO_2$ level C is in unit of ppm, said TVOC level T is in unit of ppb, said Vout is in unit of mV, $8 < a < 25$, $0.8 < b < 2$, $0.8 < c < 2$, $d = 400$, and Vout is truncated in the range of from 0 to 10000 (mV).

3. The ventilation system according to claim 1, further comprising one or more filters for reducing PM2.5 particle level in an outdoor air stream that is to be introduced into the indoor space.

4. The ventilation system according to claim 1, further comprising a first active noise reduction (ANR) module for canceling noise generated from said first air blower through destructive interference.

5. The ventilation system according to claim 1, further comprising a second motor driving a second air blower for discharging an indoor air stream from the indoor space to outdoor, and the output signal Vout is also used to vary the second motor's speed or torque.

6. The ventilation system according to claim 5, further comprising a second active noise reduction (ANR) module for canceling noise generated from said second air blower through destructive interference.

7. The ventilation system according to claim 5, wherein said outdoor air stream and said indoor air stream exchange heat through a membrane.

8. The ventilation system according to claim 1, further comprising an initial-efficiency filter, an intermediate-efficiency filter, and a high-efficiency filter arranged consecutively from upstream to downstream along flow direction of said outdoor air stream that is to be introduced into the indoor space, for reducing PM2.5 particle level in said outdoor air stream.

9. The ventilation system according to claim 8, further comprising an ozone filter for reducing ozone level in an outdoor air stream that is to be introduced into the indoor space.

10. The ventilation system according to claim 9, wherein the ozone filter is placed between the initial-efficiency filter and the intermediate-efficiency filter.

11. The ventilation system according to claim 9, wherein the ozone filter comprises cordierite honeycomb ceramic material loaded with a catalyst.

12. The ventilation system according to claim 9, wherein the ozone filter has a thickness of 20 mm.

13. A HVAC system for improving air quality of an indoor space, comprising:
   a PM2.5 particle sensor for measuring PM2.5 particle level P in the indoor space,
   a $CO_2$ sensor for measuring $CO_2$ level C in the indoor space;
   a TVOC sensor for measuring TVOC level T in the indoor space;
   a first motor driving a first air blower for introducing an outdoor air stream into the indoor space; and
   a control circuit that receives the values of P, C and T from the three sensors, and generates an output signal Vout according to the equation of Vout=(a×P+b×C+c×T)/d, a>0, b>0, c>0, and d≠0;
   wherein the output signal Vout is used to vary the first motor's speed or torque.

14. The HVAC system according to claim 13, wherein said PM2.5 particle level P is in unit of $\mu g/m^3$, said $CO_2$ level C is in unit of ppm, said TVOC level T is in unit of ppb, said Vout is in unit of mV, 8<a<25, 0.8<b<2, 0.8<c<2, d=400, and Vout is truncated in the range of from 0 to 10000 (mV).

15. The ventilation system according to claim 13, further comprising a second motor driving a second air blower for discharging an indoor air stream from the indoor space to outdoor, and the output signal Vout is also used to vary the second motor's speed or torque.

16. A process for improving air quality of an indoor space, comprising:
   measuring PM2.5 particle level P in the indoor space using a PM2.5 particle sensor;
   measuring $CO_2$ level C in the indoor space using a $CO_2$ sensor;
   measuring TVOC level T in the indoor space using a TVOC sensor;
   introducing an outdoor air stream into the indoor space using a first motor driving a first air blower;
   generating an output signal Vout by a control circuit according to the equation of Vout=(a×P+b×C+c×T)/d, wherein a>0, b>0, c>0, and d≠0, after the control circuit receives the values of P, C and T from the three sensors; and
   varying the first motor's speed or torque using the output signal Vout.

17. The process according to claim 16, wherein said PM2.5 particle level P is in unit of $\mu g/m^3$, said $CO_2$ level C is in unit of ppm, said TVOC level T is in unit of ppb, said Vout is in unit of mV, 8<a<25, 0.8<b<2, 0.8<c<2, d=400, and Vout is truncated in the range of from 0 to 10000 mV.

18. The process according to claim 16, further comprising:
   discharging an indoor air stream from the indoor space to outdoor using a second motor driving a second air blower; and
   varying the second motor's speed or torque using the output signal Vout.

19. The process according to claim 16, further comprising:
   providing one or more filters; and
   reducing PM2.5 particle level in an outdoor air stream that is to be introduced into the indoor space with said one or more filters.

20. The process according to claim 16, further comprising:
   providing an ozone filter; and
   reducing ozone level in an outdoor air stream that is to be introduced into the indoor space using said ozone filter.

* * * * *